United States Patent [19]

Baker et al.

[11] Patent Number: 5,631,347

[45] Date of Patent: May 20, 1997

[54] REDUCING GELATION OF A FATTY ACID-ACYLATED PROTEIN

[75] Inventors: Jeffrey C. Baker, Indianapolis; Jose M. Hanquier, Martinsville; Warren E. Shrader, Indianapolis, all of Ind.

[73] Assignee: Eli Lilly and Company, Indianapolis, Ind.

[21] Appl. No.: 484,545

[22] Filed: Jun. 7, 1995

[51] Int. Cl.$^6$ .............................. C07K 1/113; C07K 1/16; C07K 1/34; C07K 14/62

[52] U.S. Cl. .......................... 530/303; 530/305; 530/344; 530/345; 530/410; 530/417

[58] Field of Search ......................... 514/2, 3, 4, 12, 514/21; 530/303, 305, 344, 345, 410, 417

[56] References Cited

U.S. PATENT DOCUMENTS

| | | | |
|---|---|---|---|
| 2,626,228 | 1/1953 | Petersen et al. | 530/303 |
| 3,471,464 | 10/1969 | Bellet | 530/303 |
| 3,528,960 | 9/1970 | Haas | 530/303 |
| 3,591,574 | 7/1971 | Fenichel | 530/303 |
| 3,752,798 | 8/1973 | Amird | 530/303 |
| 3,755,569 | 8/1973 | Fenichel | 514/4 |
| 3,823,125 | 7/1974 | Grant | 530/303 |
| 3,864,325 | 2/1975 | Smyth | 530/303 |
| 3,868,356 | 2/1975 | Smyth | 530/303 |
| 3,868,357 | 2/1975 | Smyth et al. | 530/305 |
| 3,869,437 | 3/1975 | Lindsay | 530/303 |
| 3,876,623 | 4/1975 | Jackson et al. | 530/305 |
| 3,878,186 | 4/1975 | Jackson | 530/305 |
| 3,883,496 | 5/1975 | Geiger | 530/303 |
| 3,883,500 | 5/1975 | Geiger et al. | 530/303 |
| 3,884,897 | 5/1975 | Geiger et al. | 530/303 |
| 3,903,304 | 9/1975 | Groninger, Jr. et al. | 426/1 |
| 3,950,517 | 4/1976 | Lindsay et al. | 530/303 |
| 4,013,628 | 3/1977 | Obermeier | 530/303 |
| 4,014,861 | 3/1977 | Geiger et al. | 530/303 |
| 4,430,266 | 2/1984 | Frank | 530/303 |
| 4,486,458 | 12/1984 | Bradford et al. | 426/618 |
| 4,569,791 | 2/1986 | Frank et al. | 530/303 |
| 4,652,548 | 3/1987 | Chance et al. | 514/4 |
| 4,654,324 | 3/1987 | Chance et al. | 514/12 |
| 4,764,592 | 8/1988 | Massey et al. | 530/305 |
| 4,946,828 | 8/1990 | Markussen | 514/3 |
| 5,130,236 | 7/1992 | Hoffmann | 435/68.1 |
| 5,164,366 | 11/1992 | Balschmidt et al. | 514/3 |
| 5,304,473 | 4/1994 | Belagaje et al. | 435/69.7 |
| 5,504,188 | 4/1996 | Baker et al. | 530/304 |
| 5,514,646 | 5/1996 | Chance et al. | 514/3 |

FOREIGN PATENT DOCUMENTS

| | | |
|---|---|---|
| 214 826 A2 | 8/1986 | European Pat. Off. |
| 383 472 A2 | 2/1990 | European Pat. Off. |
| 1-254699 | 11/1989 | Japan. |
| 1260963 | 1/1972 | United Kingdom. |
| 1415333 | 11/1975 | United Kingdom. |
| 1492997 | 11/1977 | United Kingdom. |
| WO92/01476 | 2/1992 | WIPO. |

OTHER PUBLICATIONS

Harris, E.L.V. and Angal, S. eds. Protein Purification Methods: A Practical Approach. Oxford: IRL Press, 1989 pp. 5–9.

Anderson, et al., "The Use of Esters of N–Hydroxysuccinimide in Peptide Synthesis," *Journal of American Chemical Society*, 86:1839–1842 (1964).

Asada, et al., "Stability of Acyl Derivatives of Insulin in the Small Intestine: Relative Importance of Insulin Association Characteristics in Aqueous Solution," *Pharmaceutical Research*, 11(8):1115–1120 (1994).

Geiger, et al., "Contribution of Peptide Chemistry to our Knowledge of Insulin and Diabetes," from *Proceedings of the Symposium on Proinsulin, Insulin and C–Peptide*, Tokushima, Jul. 12–14, pp. 62–72 (1978).

Geiger, et al., "Biological Activity of Insulin Analogues Substituted at the Amino Group of B1–Phenylalanine", from *Proceedings of the Second International Insulin Symposium*, Aachen, Germany, Sep. 4–7, pp. 409–415, (1979).

Geiger, "Chemie des Insulins," *Sonderdruck* 100:111–129, (1976) (Translation Attached).

Hashimoto, et al., "Synthesis of Palmitoyl Derivatives of Insulin and Their Biological Activities," *Pharmaceutical Research*, 6(2):171–176 (1989).

Hashizume, et al., "Improvement of Large Intestinal Absorption of Insulin by Chemical Modification with Palmitic Acid in Rats," *J. Pharm. Pharmacol.*, 44:555–559(1992).

Inoue, et al., "Synthesis of a Superoxide Dismutase Derivative That Circulates Bound to Albumin and Accumulates in Tissues Whose pH is Decreased," *Biochemistry*, 28(16):6619–6624 (1989).

Kunitomo, et al., "Synthesis of Cytochrome c Derivative with Prolonged In Vivo Half–life and Determination of Ascorbyl Radicals in the Circulation of the Rat," *The Journal of Biological Chemistry*, 267(13):8732–8738 (1992).

Lapidot et al., "Use of Esters of N–hydroxysuccinimide in the Synthesis of N–acylamino Acids," *Journal of Lipid Research*, 11(8):1115–1120 (1994).

Lindsay et al., "Acetoacetylation of Insulin," *Biochem. J.*, 115:587–595 (1969).

Lindsay et al., "The Acetylation of Insulin," *Biochem. J.*, 121:737–745 (1971).

(List continued on next page.)

*Primary Examiner*—Jeffrey E. Russel
*Assistant Examiner*—Kathleen Carroll
*Attorney, Agent, or Firm*—Steven P. Caltrider; Joseph M. Skerpon; David E. Boone

[57] ABSTRACT

A method for processing a fatty acid-acylated protein, especially N-palmitoyl Lys$^{B29}$ human insulin, to reduce the incidence of gelation by conducting such processing in the presence of a citrate buffering agent as the primary buffer which method allows such processing to be conducted at higher protein concentrations and with less temperature control than would otherwise be possible in the absence of the citrate buffer.

20 Claims, No Drawings

OTHER PUBLICATIONS

MacIntyre et al., "Information About Insulin by Chemical and Enzymatic Modifications," *Molecular Endocrinology*, Proceedings of Endocrinology '77 held at the Royal College of Physicians, London, England Jul. 11–15, pp. 27–42 (1977).

Muranishi, et al., "Trials of Lipid Modification of Peptide Hormones for Intestinal Delivery," *Journal of Controlled Release*, 19:179–188 (1992).

Riordan, et al., "Acetylation," *Methods of Enzymology*, 25:494–499 (1972).

Rösen et al., "A1–Modified Insulins: Receptor Binding and Biological Activity," Insulin Chemistry, Structure and Function of Insulin and Related Hormones from Proceedings of the Second International Insulin Symposium, Aachen, Germany, Sep. 4–7, pp. 403–408 (1979).

Scheider, "Ligand–Independent Activated State of Serum Albumin for Fatty Acid Binding," *Journal of Physical Chemistry*, 84(8):925–928 (1980).

REDUCING GELATION OF A FATTY ACID-ACYLATED PROTEIN

BACKGROUND OF THE INVENTION

1. Field of the Invention

The present invention is broadly directed to a method for reducing the onset or incidence of gelation during the processing and purification of fatty acid acylated-proteins, especially fatty acid-acylated proinsulins, fatty acid-acylated insulins or fatty acid-acylated insulin analogs. More particularly, the present invention relates to a method of processing and purifying such acylated proinsulins, insulins and insulin analogs, and most especially N-palmitoyl Lys$^{B29}$ human insulin, in the presence of a citrate buffering agent.

2. Description of Related Art

It has long been a goal of insulin therapy to mimic the pattern of endogenous insulin secretion in normal individuals. The daily physiological demand for insulin fluctuates and can be separated into two phases: (a) the absorptive phase requiting a pulse of insulin to dispose of the meal-related blood glucose surge, and (b) the post-absorptive phase requiring a sustained amount of insulin to regulate hepatic glucose output for maintaining optimal fasting blood glucose. Accordingly, effective therapy generally involves the combined use of two exogenous insulins: a fast-acting meal time insulin provided by bolus injections and a long-acting basal insulin administered by injection once or twice daily.

Recently, a class of acylated insulins has shown promise for use as a long-acting basal insulin therapy. These acylated insulins are prepared by acylating, selectively with an activated fatty acid derivative, the free amino group(s) of a monomeric insulin, including a proinsulin, normal insulin and certain insulin analogs. Useful fatty acid derivatives include reactive fatty acid-type compounds having at least a six (6) carbon atom chain length and particularly those fatty acid derivatives having 8 to 21 carbon atoms in their chain. Mono-acylated normal human insulin, acylated with a palmitic acid derivative, is a particularly promising candidate. Insulins falling within this category are described in Japanese patent application 1-254,699.

One problem encountered with these fatty acid-acylated insulins is that they show a pronounced tendency to gel under conditions commonly encountered after their preparation, particularly during their subsequent purification and concentration. While the reasons contributing to this gelation phenomenon are not understood, it has been observed that solutions of these fatty acid-acylated insulins, and in particular aqueous acetonitrile solutions of N-palmitoyl Lys$^{B29}$ human insulin, undergo a visible physical change under commonly used conditions of temperature, pH and protein concentration, in the presence of buffers normally used, such as glycine and acetic acid. For example, aqueous solutions of N-palmitoyl Lys$^{B29}$ human insulin at concentrations greater than 4 mg/ml and containing above 20–30% acetonitrile have shown a strong tendency to gel quickly at room temperature in the presence of 20 mM glycine as the buffering agent. The gelling that occurs interferes significantly with proper processing and ultimate purification and concentration of the protein. Indeed, when this condition occurs, the composition is difficult, if not impossible to pump or otherwise handle. This results in a loss of facilities and equipment use. While a similar gelation phenomenon has sometimes been encountered when processing normal insulin, it generally has been avoided using judicious process control measures. Unfortunately, the fatty acid-acylated insulins appear to be much less forgiving, such that the gelation phenomenon poses a significant problem to commercial scale processing of these fatty acid-acylated proteins.

The present invention is based on the surprising discovery that by processing these fatty acid-acylated insulins in the presence of a citrate buffering agent as the primary buffer in the process stream, particularly a process stream containing a polar organic solvent such as acetonitrile, the tendency of these fatty acid-acylated insulins to gel, and especially N-palmitoyl Lys$^{B29}$ human insulin, is greatly reduced.

The present invention therefore provides a method for processing an aqueous solution of such fatty acid-acylated insulins at higher protein concentrations and with less temperature control than would otherwise be appropriate in the absence of the citrate buffer. The present invention also provides aqueous solutions of fatty acid-acylated proteins having a reduced tendency to gel.

DESCRIPTION OF THE INVENTION

All amino acid abbreviations used in this disclosure are those accepted by the United States Patent and Trademark Office as set forth in 37 C.F.R. §1.822(B)(2).

The terms "insulin" and "normal insulin" as used herein mean human insulin, pork insulin, or beef insulin. Insulin possesses three free amino groups: B$^1$-Phenylalanine, A$^1$-Glycine, and B$^{29}$-Lysine. The free amino groups at positions A$^1$ and B$^1$ are α-amino groups. The free amino group at position B$^{29}$ is an ε-amino group.

The term "proinsulin" as used herein is a properly cross-linked protein of the formula:

B-C-A wherein:

A is the A chain of insulin or a functional derivative thereof;

B is the B chain of insulin or a functional derivative thereof having an ε-amino group; and C is the connecting peptide of proinsulin. Preferably, proinsulin is the A chain of human insulin, the B chain of human insulin, and C is the natural connecting peptide. When proinsulin is the natural sequence, proinsulin possesses three free amino groups: Phenylalanine(1) (α-amino group), Lysine(29) (ε-amino group) and Lysine(64) (ε-amino group).

The term "insulin analog" as used herein is a properly cross-linked protein exhibiting insulin activity of the formula:

A-B wherein:

A is the A chain of insulin or a functional derivative of the insulin A chain; and B is the B chain of insulin or a functional derivative of the insulin B chain having an ε-amino group and at least one of A or B contains an amino acid modification from the natural sequence.

Preferred insulin analogs include insulin wherein:

the amino acid residue at position B$^{28}$ is Asp, Lys, Leu, Val, or Ala;

the amino acid residue at position B$^{29}$ is Lys or Pro;

the amino acid residue at position B$^{10}$ is His or Asp;

the amino acid residue at position $B^1$ is Phe, Asp, or deleted alone or in combination with a deletion of the residue at position $B^2$;

the amino acid residue at position $B^{30}$ is Thr, Ala, or deleted; and the amino acid residue at position $B^9$ is Ser or Asp; provided that either position $B^{28}$ or $B^{29}$ is Lys.

In standard biochemical terms known to the ordinarily skilled artisan the preferred insulin analogs are $Lys^{B28}Pro^{B29}$-human insulin ($B^{28}$ is Lys; $B^{29}$ is Pro); $Asp^{B28}$-human insulin ($B^{28}$ is Asp); $Asp^{B1}$-human insulin, $Arg^{B31,B32}$-human insulin, $Asp^{B10}$-human insulin, $Arg^{A0}$-human insulin, $Asp^{B1},Glu^{B13}$-human insulin, $Ala^{B26}$-human insulin, and $Gly^{A21}$-human insulin.

The term "acylating" means the introduction of one or more acyl groups covalently bonded to the free amino groups of the protein.

The term "fatty acid" means a saturated or unsaturated $C_6$–$C_{21}$ fatty acid.

The term "activated fatty acid ester" means a fatty acid which has been activated using general techniques such as described in *Methods of Enzymology*, 25:494–499 (1972) and Lapidot el al., in *J. of Lipid Res.*, 8:142–145 (1967), the disclosures of which are incorporated herein by reference. The preferred fatty acids are saturated and include myristic acid ($C_{14}$), pentadecylic acid ($C_{15}$), palmitic acid($C_{16}$), heptadecylic acid ($C_{17}$) and steric acid ($C_{18}$). Most preferably, the fatty acid is palmitic acid. Activated fatty acid esters include derivatives of agents such as hydroxybenzotriazide (HOBT), N-hydroxysuccinimide and derivatives thereof. The preferred activated ester is N-succinimidyl palmitate.

The term "cross-link" means the formation of disulfide bonds between cysteine residues. A properly cross-linked proinsulin, insulin or insulin analog contains three disulfide bridges. The first disulfide bridge is formed between the cysteine residues at positions 6 and 11 of the A-chain. The second disulfide bridge links the cysteine residues at position 7 of the A-chain to the cysteine at position 7 of the B-chain. The third disulfide bridge links the cysteine at position 20 of the A-chain to the cysteine at position 19 of the B-chain.

The term "aqueous" includes cosolvent systems as well as use of water only as a solvent.

The present invention relates to an improved method for processing a fatty acid-acylated protein, particularly a fatty acid-acylated proinsulin, a fatty acid-acylated insulin or a fatty acid-acylated insulin analog, while reducing the onset of gelation. The invention particularly pertains to processing a fatty acid-acylated protein through protein modification, protein enrichment or concentration and protein purification operations, while reducing the onset of gelation. The invention is characterized by having such processing, and especially such modification, enrichment and purification operations, conducted using an aqueous solution of the acylated protein containing a citrate buffering agent and/or, where appropriate, having such operations conducted in the presence of an aqueous solution containing a citrate buffering agent. Preferred acylated proteins processed using the method of the present include N-acylated $Lys^{B29}$ human insulin, preferably N-palmitoyl $Lys^{B29}$ human insulin and B28-$N^\epsilon$-acylated-$Lys^{B28}Pro^{B29}$-human insulin (B28 is acylated Lys and B29 is Pro), preferably B28-$N^\epsilon$-palmitoyl-$Lys^{B28}Pro^{B29}$-human insulin.

The present invention also relates to a gelation resistant, fatty acid-acylated protein solution comprising a fatty acid-acylated protein and an amount of a citrate buffering agent sufficient to retard gelling of the fatty acid-acylated protein.

Proinsulin, insulin and insulin analogs used to prepare the fatty acid-acylated proteins that are the principal focus of the present invention can be prepared by any of a variety of recognized peptide synthesis techniques including classical (solution) methods, solid phase methods, semi-synthetic methods, and more recent recombinant DNA methods. For example, Chance et al., U.S. patent application Ser. No. 07/388,201, now abandoned, EPO publication number 383 472, Brange et at., EPO 214 826, and Belagaje et al., U.S. Pat. No. 5,304,473 disclose the preparation of various proinsulin and insulin analogs and are herein incorporated by reference. The A and B chains of the insulin analogs of the present invention may also be prepared via a proinsulin-like precursor molecule using recombinant DNA techniques. See Frank et al., Peptides: Synthesis-Structure-Function, *Proc. Seventh Am. Pept. Symp.*, Eds. D. Rich and E. Gross (1981) which is incorporated herein by reference.

Generally, the proinsulin, insulin and insulin analogs are acylated by reacting them with an activated fatty acid derivative, such as an activated fatty acid ester. The acylation of normal insulin with a fatty acid is disclosed in Japanese patent application 1-254,699. See also Hashimoto et at., *Pharmaceutical Research*, 6: 171–176 (1989). These disclosures are incorporated herein by reference.

Preferably, the acylation is conducted under basic conditions, i.e., at a pH greater than 9.0 and preferably about 10.5, in a polar solvent. While the reaction can be conducted in a wholly organic polar solvent using a base having an aqueous pKa of greater than or equal to 10.75, we generally prefer a mixed organic and aqueous solvent for the reaction medium. Preferred bases are tetramethylguanidine, diisopropylethylamine or tetrabutylammonium hydroxide. One particularly suitable solvent has been acetonitrile and water, containing about 50% acetonitrile. Other polar solvents include dimethylsulfoxide, dimethylformamide and the like. Cosolvent systems also include acetone and water, isopropyl alcohol and water, and ethanol and water. Time and temperature conditions suitable for conducting the reactions are not narrowly critical. A temperature of 0° to 40° C. and a reaction time of 15 minutes to 24 hours should generally be suitable. A particularly preferred way of preparing such fatty acid-acylated insulins is described in copending U.S. application Ser. No. 08/341231 filed Nov. 17, 1994, the disclosure of which is incorporated herein by reference.

Once the acylation reaction is complete, the reaction mixture typically is diluted with water and, in accordance with one embodiment of the present invention, citric acid can be added to neutralize the alkalinity. The resulting citrate acts as a buffering agent for subsequent processing, including enrichment and purification operations. In this embodiment, the citric acid is supplied as an aqueous solution to the acylated protein and serves to lower the solution pH to below the isoelectric point (isoelectric pH) of the acylated insulin. Normally at this point, the protein is in a properly buffered aqueous solution for further processing. Such processing particularly includes purification by standard chromatographic methods such as reverse phase or hydrophobic chromatography, concentration by crossflow filtration, solvent exchange by ultrafiltration and the like.

For acylated proinsulin, acylated insulin and acylated insulin analogs, particularly N-palmitoyl $Lsy^{B29}$ human insulin and B28-$N^\epsilon$-palmitoyl-$Lys^{B28}Pro^{B29}$-human insulin, the pH normally should be adjusted to below about 3.0, and preferably to between about 1.5 and 2.5, using the aqueous citric acid as-needed. If needed, the pH also can be readjusted with a base, such as sodium hydroxide, to keep it within the desired range. A pH of about 2.5 has been found to be suitable for processing N-palmitoyl $Lsy^{B29}$ human insulin.

In the broad practice of the present invention, it is contemplated that the acylated protein can be subjected to a wide variety of chemical treatments, physical separations and purification operations, including chromatographic treatment and crossflow filtration such as for purifying the protein composition, concentrating the protein solution or for solvent exchange, and chemical and enzymatic treatments. All such operations are preferably conducted in the presence of the citrate buffering agent of the present invention to reduce the onset of gelation. Protein processing contemplated by the present invention particularly includes purification by standard chromatographic methods such as reverse-phase chromatography, hydrophobic chromatography and the like, and protein concentration by ultrafiltration and similar processes. Protein processing is also intended to encompass the retention of the protein solution in holding tanks and the like preparatory to such purification and concentration steps.

In accordance with the present invention, the citrate buffering agent also can be established in the aqueous acylated insulin solution, by neutralizing a dilute alkaline solution, such as the fatty acid-acylated insulin solution recovered from the acylation reaction, with another acid, such as hydrochloric acid or acetic acid, followed by addition of a citrate salt. Suitable citrate salts include monosodium citrate, disodium citrate, monoammonium citrate, and diammonium citrate for example. As used herein, the phrase "citrate buffering agent" includes any compound that introduces citrate ions into the aqueous protein solution.

In order to impart a gel-retarding character to the acylated insulin solution, the solution should be provided with a citrate ion concentration of at least about 25 mM, and preferably about 50 mM. While higher concentrations can be used, we recommend a practical upper limit of about 1.0M to avoid complicating possible processing options and eventual protein purification steps. Similarly, for best performance the pH of the solution should be maintained within the range of about 1.5 and 3.0 during processing. Generally a pH of about 2.5 should be suitable.

Thereafter, to reduce the likelihood of gelation, all processing of the fatty acid-acylated protein solution, especially aqueous fatty acid-acylated insulin solutions containing an organic polar solvent such as acetonitrile, and including various protein purification and protein concentration steps, is conducted in the presence of the citrate buffer. Such processing steps generally are directed to the ultimate isolation of the acylated protein, such as a fatty acid-acylated insulin, usually as a dry powder.

For instance, the fatty acid-acylated insulin reaction product may, prior to recovery of a powdered product, be purified and enriched through sequential steps of chromatography and ultrafiltration. In order to reduce the incidence of gelation during such processing, these purification steps are conducted in aqueous solution in the presence of a citrate buffering agent.

For example, in the case of a chromatographic separation, the protein solution recovered from the acylation reaction, possibly in an organic solvent, can be applied to the chromatograpic column and then would be developed using an aqueous mobile phase or aqueous eluent containing at least 25 mM of citrate buffering agent and preferably about 50 mM of citrate buffering agent. As recognized by those skilled in the art, the eluent would include an organic polar solvent such as acetonitrile whose concentration likely would change during development of the column (gradient elution) to facilitate elution of the protein from the column. Although not essential, it also is preferred that the protein solution to be resolved be introduced into the column in a solution containing a citrate buffer.

In the case of an ultrafiltration operation, in addition to providing the insulin solution to the ultrafiltration membrane in a citrate buffered solution, any ultrafiltration wash solution also should contain at least 25 mM of citrate buffering agent and preferably 50 mM of citrate.

After these purification and enrichment steps, the aqueous solution of the purified fatty acid-acylated protein, particularly a fatty acid-acylated proinsulin, a fatty acid-acylated insulin or a fatty acid-acylated insulin analog, can be processed to recover the soluble protein as a powder. In the broad practice of the present invention, any procedure for recovering the acylated protein as a powder, including lyophilization (freeze drying), crystallization or precipitation techniques, can be used. The present invention is not limited to the way of isolating and recovering the acylated protein in powder form.

Acylated insulin and acylated insulin analog powders which may ultimately be prepared using the process of the present invention are useful for preparing pharmaceutical compositions used in insulin therapy, i.e. for administering to a patient in need thereof (i.e. a patient suffering from hyperglycemia). Such pharmaceutical compositions may contain an effective amount of the fatty acid-acylated insulin or fatty acid-acylated insulin analog in an aqueous solution with a citrate buffering agent as one component, in combination with one or more pharmaceutically acceptable excipients or carriers. For these purposes, the pharmaceutical compositions may typically be formulated so as to contain about 100 units per mL or similar concentrations containing an effective amount of the fatty acid-acylated insulin or fatty acid-acylated insulin analog. These compositions are typically, though not necessarily, parenteral in nature and may be prepared by any of a variety of techniques using conventional excipients or carriers for parenteral products which are well known in the art. See, for example, *Remington's Pharmaceutical Sciences*, 17th Edition, Mack Publishing Company, Easton, Pa., U.S.A. (1985) which is incorporated herein by reference. For example, dosage forms for parenteral administration may be prepared by suspending or dissolving the desired amount of an insulin powder in a non-toxic liquid vehicle suitable for injection such as an aqueous medium and sterilizing the suspension or solution. Alternatively, a measured amount of the insulin powder may be placed in a vial; and the vial and its contents sterilized and sealed. An accompanying vial or vehicle can be provided for purposes of mixing prior to administration.

Pharmaceutical compositions adapted for parenteral administration employ diluents, excipients and carriers such as water and water-miscible organic solvents such as glycerin, sesame oil, groundnut oil, aqueous propylene glycol, N,N-dimethylformamide and the like. Examples of such pharmaceutical compositions include sterile, isotonic, aqueous saline solutions of the insulin that can be buffered with a pharmaceutically acceptable buffer and that are pyrogen free. Additionally, the parenteral pharmaceutical formulation may contain preservatives such as metacresol, other agents to adjust pH of the final product such as sodium hydroxide or hydrochloric acid and stabilizers such as zinc salts.

The following examples are presented to illustrate and explain the invention. While the invention is illustrated by reference to the processing of solutions containing N-palmitoyl Lys$^{B29}$ human insulin, the scope of the invention should not be considered as being limited to these examples. Unless otherwise indicated, all references to pans

EXAMPLE 1

An aqueous solution of a fatty acid-acylated Biosynthetic Human Insulin (N-palmitoyl Lys$^{B29}$ human insulin) containing approximately 12.5% by volume acetonitrile and 12.5 mM of boric acid, at a pH of 2.5 and having a temperature of 4° C., was charged onto a low performance reverse phase chromatography column. The column was packed with SP20SS resin, available from Mitsubishi, which was pre-equilibrated with an aqueous solution containing 10% by volume acetonitrile and 50 mM of citric acid at a pH of 2.5 and also having a temperature of 4° C. The acylated insulin was charged onto the resin at a ratio of about 7 grams of insulin per liter of packed resin. After loading the column, the column was washed with one (1) column volume of an aqueous buffer solution containing 25% by volume acetonitrile and 50 mM citric acid and having a pH of 2.5. The loaded column thereafter was eluted under a linear gradient of from 25% to 55% by volume acetonitrile in an aqueous 50 mM citric acid solution having a pH of 2.5 and a temperature of 4° C. The column was eluted with five (5) column volumes of eluate. Fractions were collected and pooled accordingly.

One portion of the resulting mainstream was held at 4° C. for two weeks, and another portion was held at 25° C. for 12–16 hours without any visible signs of gelation in either solutions. Comparative Example 1

A similar aqueous solution of fatty acid-acylated Biosynthetic Human Insulin (N-palmitoyl Lys$^{B29}$ human insulin) containing approximately 12.5% by volume acetonitrile and 12.5 mM of boric acid, at a pH of 2.5 and having a temperature of 4° C., was charged onto a low performance reverse phase chromatography column. In this case, the column also was packed with the SP20SS resin, but was pre-equilibrated instead with an aqueous solution containing 10% by volume acetonitrile and 20 mM of glycine at a pH of 2.8–3.2. Using the same insulin loading ratio, washing procedure and elution protocol, fractions were collected and pooled accordingly. In this case, one portion of the resulting mainstream, which was held at 4° C. gelled with in three (3) days, while another fraction of the mainstream held at 25° C. gelled within an hour. The purifies of the mainstreams collected with the different buffers in Example 1 and Comparative Example 1 were not significantly different.

EXAMPLE 2

An aqueous solution of a fatty acid-acylated Biosynthetic Human Insulin (N-palmitoyl Lys$^{B29}$ human insulin) containing approximately 32% by volume acetonitrile and 50 mM of citrate at a pH of 2.45 was ultrafiltered at a crossflow rate of 1.5 to 2.0 l/min, under a transmembrane pressure of 10 to 40 psi, at a temperature in the range of 5°–13° C. through a MILLIPORE® 5000 molecular weight cut-off (MWCO) membrane (one square foot) to increase its concentration from about 4.0 mg/ml to about 15 mg/ml. Not only did no gel form during the ultrafiltration, but the retentate, containing 15 mg/ml of the acylated insulin and approximately 32% by volume acetonitrile was stored for two weeks at 5° C. and showed no signs of gel formation.

Comparative Example 2

An aqueous solution of a fatty acid-acylated Biosynthetic Human Insulin (N-palmitoyl Lys$^{B29}$ human insulin) containing 32% acetonitrile and 20 mM of glycine at a pH of 2.5 was ultrafiltered with the permeate recycled to the feed vessel so that the solution was not concentrated, using the same flow and transmembrane pressure conditions of Example 2, at a temperature in the range of 9°–16° C. and at a protein concentration of 4.5 mg/ml. The solution was filtered for one hour through a MILLIPORE® 5000 molecular weight cut-off (MWCO) membrane (one square foot). Storage of the retentate, containing 4.5 mg/ml of acylated insulin, for two days at 5° C. resulted in the formation of large clumps of gel. A sample of the original solution, not subjected to processing through the ultrafiltration device, did not gel under the same storage conditions.

EXAMPLE 3

An aqueous solution of a fatty acid-acylated Biosynthetic Human Insulin (N-palmitoyl Lys$^{B29}$ human insulin) containing about 35 to 40% by volume acetonitrile and 50 mM of citrate at a pH of 2.45 was ultrafiltered at a crossflow rate of about 1.5 to 2.0 l/min, under a transmembrane pressure of 10 to 40 psi, and at a temperature in the range of 5°–13° C. through a MILLIPORE® 5000 molecular weight cut-off (MWCO) membrane (one square foot) to increase its concentration from about 7.5 mg/ml to about 70 mg/ml. Gel did not form during the ultrafiltration.

Comparative Example 3

An aqueous solution of a fatty acid-acylated Biosynthetic Human Insulin (N-palmitoyl Lys$^{B29}$ human insulin) containing about 35 to 40% by volume acetonitrile and 20 mM of glycine at a pH of 2.5 was ultrafiltered through an Amicon 3000 MWCO ultrafiltration membrane at similar crossflow and transmembrane pressure conditions to those of Example 3, and at a temperature in the range of 5°–10° C. to increase the concentration from 1.5 mg/ml. As the concentration of acylated insulin reached about 6 mg/ml, the solution became cloudy. By the time the concentration should have reached 10 mg/ml, the solution gelled. By diluting the initial acylated insulin solution to about 20% by volume acetonitrile, it was possible to concentrate the protein to 10 mg/ml without gelation.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention. For example, although the present invention has been described with particularity in the context of the purification and ultimate recovery of a fatty acid-acylated proinsulin, a fatty acid-acylated insulin and a fatty acid-acylated insulin analog, and especially for processing N-palmitoyl Lys$^{B29}$ human insulin, it is thought that the invention will be applicable to other fatty acid-acylated proteins.

We claim:

1. In a method of processing an aqueous solution of a fatty acid-acylated protein, the improvement comprising conducting the processing of said protein in the presence of an aqueous solution containing a sufficient amount of a citrate buffering agent to retard gelation of the acylated protein.

2. The method of claim 1 wherein said fatty acid-acylated protein is selected from the group consisting of a fatty acid-acylated proinsulin, a fatty acid-acylated insulin and a fatty acid-acylated insulin analog.

3. The method of claim 2 wherein said aqueous solution has a citrate concentration of at least 25 mM.

4. The method of claim 3 wherein said aqueous solution has a pH of 1.5 to 3.0.

5. The method of claim 4 wherein said fatty acid-acylated protein is selected from the group consisting of N-palmitoyl Lys$^{B29}$ human insulin and B28-N$^\epsilon$-palmitoyl-Lys$^{B28}$Pro$^{B29}$-human insulin.

6. In a method for purifying an aqueous solution of a fatty acid-acylated protein by chromatographic separation, the improvement comprising eluting said fatty acid-acylated protein during said chromatographic separation using an aqueous elution solution containing a sufficient amount of a citrate buffering agent to retard gelation of the acylated protein.

7. The method of claim 6 wherein said fatty acid-acylated protein is selected from the group consisting of a fatty acid-acylated proinsulin, a fatty acid-acylated insulin and a fatty acid-acylated insulin analog.

8. The method of claim 7 wherein said aqueous elution solution has a citrate concentration of at least 25 mM.

9. The method of claim 8 wherein said aqueous elution solution has a pH of 1.5 to 3.0.

10. The method of claim 9 wherein said fatty acid-acylated protein is selected from the group consisting of N-palmitoyl Lys$^{B29}$ human insulin and B28-N$^\epsilon$-paimitoyl-Lys$^{B28}$Pro$^{B29}$-human insulin.

11. In a method for concentrating an aqueous solution of a fatty acid-acylated protein by crossflow filtration, the improvement comprising feeding said fatty acid-acylated protein to a filtration membrane as an aqueous solution containing a sufficient amount of a citrate buffering agent to retard gelation of the acylated protein.

12. The method of claim 11 wherein said fatty acid-acylated protein is selected from the group consisting of a fatty acid-acylated proinsulin, a fatty acid-acylated insulin and a fatty acid-acylated insulin analog.

13. The method of claim 12 wherein said aqueous solution has a citrate concentration of 25 mM.

14. The method of claim 13 wherein said aqueous solution has a pH of 1.5 to 3.0.

15. The method of claim 14 wherein said fatty acid-acylated protein is selected from the group consisting of N-palmitoyl Lys$^{B29}$ human insulin and B28-N$^\epsilon$-palmitoyl-Lys$^{B28}$Pro$^{B29}$-human insulin.

16. A gelation resistant, aqueous solution of a fatty acid-acylated protein comprising a fatty acid-acylated protein and an amount of a citrate buffering agent sufficient to retard gelling of the fatty acid-acylated protein.

17. The protein solution of claim 16 wherein said fatty acid-acylated protein is selected from the group consisting of a fatty acid-acylated proinsulin, a fatty acid-acylated insulin and a fatty acid-acylated insulin analog.

18. The protein solution of claim 17 wherein said aqueous solution has a citrate concentration of 25 mM.

19. The protein solution of claim 18 wherein said aqueous solution has a pH of 1.5 to 3.0.

20. The protein solution of claim 19 wherein said fatty acid-acylated protein is selected from the group consisting of N-palmitoyl Lys$^{B29}$ human insulin and B28-N$^\epsilon$-palmitoyl-Lys$^{B28}$Pro$^{B29}$-human insulin.

* * * * *